United States Patent [19]

Findlay et al.

[11] Patent Number: 4,713,327

[45] Date of Patent: Dec. 15, 1987

[54] DETERMINATION OF TOTAL CREATINE KINASE OR AN ISOENZYME WITH A MULTILAYER ANALYTICAL ELEMENT

[75] Inventors: John B. Findlay, Rochester; Annie L. Wu, Penfield; Gary E. Norton, Rochester, all of N.Y.

[73] Assignee: Eastman Kodak Company, Rochester, N.Y.

[21] Appl. No.: 729,331

[22] Filed: May 1, 1985

[51] Int. Cl.$^4$ .................... C12Q 1/50; C12M 1/38; G01N 33/50

[52] U.S. Cl. ........................ 435/17; 422/54; 435/291

[58] Field of Search ............ 435/17, 291; 422/56, 422/57; 436/528, 535, 169

[56] References Cited

U.S. PATENT DOCUMENTS

| | | | |
|---|---|---|---|
| 3,929,580 | 12/1975 | Fergione et al. | 195/99 |
| 3,992,158 | 11/1976 | Przybylowicz et al. | 23/253 |
| 4,042,335 | 8/1977 | Clément | 23/253 |
| 4,066,403 | 1/1978 | Bruschi | 23/230 B |
| 4,144,306 | 3/1979 | Figueras | 422/56 |
| 4,237,044 | 12/1980 | Wurzburg et al. | 260/112 B |
| 4,547,461 | 10/1985 | Esders et al. | 435/17 |

FOREIGN PATENT DOCUMENTS 116307 1/1984 European Pat. Off.

*Primary Examiner*—David M. Naff
*Attorney, Agent, or Firm*—J. Lanny Tucker

[57] ABSTRACT

A multilayer analytical element for the determination of creatine kinase comprises a support having thereon, in order and in fluid contact, a registration layer and an isotropically porous spreading layer. The registration layer contains a binder material at a coverage of at least about 8 g/m$^2$, which coverage improves the stability and keeping properties of the element in high humidity environments. This element is useful in an analytical method for determining total creatine kinase or any one of its isoenzymes, e.g. creatine kinase-MB.

19 Claims, No Drawings

DETERMINATION OF TOTAL CREATINE KINASE OR AN ISOENZYME WITH A MULTILAYER ANALYTICAL ELEMENT

FIELD OF THE INVENTION

The present invention relates to clinical chemistry. In particular, it relates to a method for the determination of total creatine kinase or of one of its isoenzymes in aqueous liquids, e.g. biological fluids. This invention also relates to a multilayer analytical element useful in such method.

BACKGROUND OF THE INVENTION

The determination of the activity of creatine kinase (abbreviated herein to CK, but also known as creatine phosphokinase, CPK, or ATP:creatine phosphotransferase E.C.2.7.3.2.) in human serum is considered one of the most sensitive laboratory methods for diagnosing diseases of skeletal muscles, such as diseases of the myocardium. Total CK determination is useful, for example, for diagnosis of progressive muscular dystrophy, dermatomyositis and especially myocardial infarctions.

Conventional assays for total creatine kinase (i.e. assay for all isoenzymes) generally use either forward or reverse reaction illustrated by the following equation:

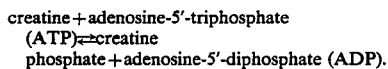

creatine+adenosine-5'-triphosphate (ATP)⇌creatine phosphate+adenosine-5'-diphosphate (ADP).

Both the forward and reverse reactions have been used in analytical procedures, but use of the reverse reaction is preferred because it is about six times faster than the forward reaction. The presence of ATP can then be determined by a number of colorimetric or potentiometric methods.

CK occurs in human body fluids and tissue in the form of three isoenzymes: CK-MM, for example in muscles, CK-BB, for example in the brain, and CK-MB, for example in the myocardium. The CK activity occurring in healthy human blood serum is normally due to the CK-MM isoenzyme, because CK-BB does not generally pass into the blood stream. In a healthy individual, CK-MB is generally restricted to certain organs, e.g. the myocardium. However, when the myocardium is damaged, as in the case of a cardiac infarction, CK-MB is released into the blood serum and can be detected therein.

A potential difficulty encountered in methods for determining CK-MB in biological fluids is interference from the other two isoenzymes. For practical puspores, the amount of CK-BB in the fluid is considered negligible in most determinations. In methods for determining CK-MB, it is known to precipitate or inhibit the M subunit with specific antibodies to eliminate the interference of CK-MM and then to measure the remaining hybrid isoenzyme CK-MB.

A relatively recent contribution to clinical chemistry was the development of dry multilayer analytical elements useful for the assay of liquids. Such elements are described, for example, in U.S. Pat. No. 3,992,158 (issued Nov. 16, 1976 to Przybylowicz et al). These elements generally have a support on which is coated a registration layer and a porous spreading layer. The registration layer generally comprises a polymeric binder (e.g. gelatin) and optionally, one or more other components, including reagents, buffers, surfactants, etc.

A number of multilayer analytical elements have been designed for various assays and used commercially, including an element useful for the determination of total CK. Such elements have generally been prepared with about 5.5 g/m² or less (dry coverage) of binder material in the registration layer in order to make as thin an element as possible and to reduce manufacturing costs.

It has been found, however, that such elements have reduced stability and room temperature keeping properties in high humidity environments, i.e. 50% relative humidity at 25° C. Moreover, manufacturing processes used in making such analytical elements are necessarily carried out in this type of environment. The reduced stability under such conditions is a serious problem. It limits the flexibility in handling the elements by both the manufacturer and the user. The manufacturer must try to limit the amount of time the element is subject to high humidity. Further, if a user accidentally leaves the element out of the freezer compartment it is normally kept in prior to use, the element is likely to give erroneous results in the assay.

It would be desirable to improve the stability, and hence the room temperature keeping properties, of analytical elements in high humidity environments.

SUMMARY OF THE INVENTION

We have found a means for improving the stability of the creatine kinase multilayer analytical elements described above and of overcoming the problems associated with known creatine kinase elements. More specifically, we have found that if the coverage of the binder material in the registration layer of such elements is increased considerably, that is, to at least about 8 g/m² (dry weight), the element is significantly more stable under high humidity conditions. As a consequence, the element has improved room temperature keeping properties under the high humidity conditions generally encountered in manufacturing. The element is also less susceptible to inaccurate results because of user mistakes in element storage.

Therefore, in accordance with this invention, a multilayer analytical element for the determination of total creatine kinase or one of its isoenzymes comprises a substrate for creatine kinase and an indicator composition which provides a detectable change in response to the reaction of the substrate with creatine kinase or its isoenzyme. The element also comprises a support having thereon, in order and in fluid contact, a registration layer containing a binder material at a coverage of at least about 8 g/m², and an isotropically porous spreading layer.

This invention also provides a method for the determination of total creatine kinase or one of its isoenzymes in an aqueous liquid. This method comprises the steps of:

(A) contacting a sample of the liquid with the analytical element described above, and (B) determining the resulting detectable change.

DETAILED DESCRIPTION OF THE INVENTION

The present invention relates to the determination (qualitative, i.e. mere detection, semi-quantitative or quantitative measurement) of total creatine kinase or a creatine kinase isoenzyme in aqueous liquids. In particular, the invention can be used to assay biological fluids of either animals or humans, but preferably of humans. Such fluids include, but are not limited to, whole blood, plasma, sera, lymph, bile, urine, spinal fluid, sputum, perspiration and the like as well as stool secretions. It is also possible to assay fluid preparations of human or animal tissue such as skeletal muscle, heart, kidney, lungs, brains, bone marrow, skin and the like. The preferred biological fluid for practice of the invention is human blood serum. Advantageously, the test sample need not be diluted, but can be diluted if desired.

In a preferred embodiment, the present invention relates to an immunochemical method for selectively determining an isoenzyme of creatine kinase, e.g. creatine kinase-MB, in a biological fluid which also possibly contains CK-MM and CK-BB. The other isoenzymes can be similarly determined. Generally, the method of this invention comprises contacting the liquid to be assayed with the analytical element of this invention, the details of which are provided below. Prior to or simultaneously with that contact, for an assay of an isoenzyme, the liquid sample is contacted with one or more antibodies which are capable of either preferentially reacting with or preferentially inhibiting the enzymatic activity of the isoenzymes not of interest, e.g. the M subunits in the CK-MM and CK-MB isoenzymes present in the sample. In this example, the B subunit of the CK-MB isoenzyme is ideally uneffected by the presence of the antibodies, and therefore, are free to react in any of a number of reaction schemes to produce a detectable change. The amount of CK-BB is generally considered negligible in such assays. The detectable change produced is then directly correlated to the amount of CK-MB isoenzyme in the fluid sample.

The detectable change can be either a potentiometric change or an optical density change as long as the change results from the reaction of creatine phosphate or its reaction product according to the reaction (1) in the forward direction:

(1)

In its simplest form, the assay can measure either the disappearance of creatine phosphate, or the appearance of creatine as described, for example, in PCT application No. 82/2213 (published July 8, 1982).

Generally, however, reaction (1) is coupled with one or more other enzymatic reactions which provide a potentiometric change or an optical density change as a result of further reaction of ATP or its reaction product. If a potentiometric change is generated, creatine kinase or its isoenzyme is determined by measuring the rate of change in electrical output with an ion-sensing electrode. For example, U.S. Pat. No. 4,042,462 (issued Aug. 16, 1977 to Johnson et al) describes a potentiometric means for measuring the uptake of oxygen as a result of the following sequence of enzymatic reactions (2)–(4) used in combination with reaction (1) above:

(2)

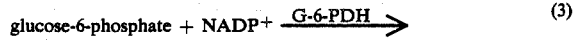

(3)

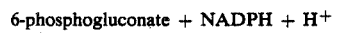

-continued

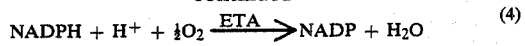

(4)

wherein NADP (NADPH) is nicotinamide adenine dinucleotide phosphate (same, reduced form), G-6-DPH is glucose-6-phosphodehydrogenase and ETA is an electron transfer agent.

Preferably, CK or its isoenzyme is determined in the present invention by measuring an optical density change. This change can be colorimetric, fluorometric, or photometric, and is meant to include the rate of appearance of light, the rate of increase or decrease in optical density, and the rate of a shift in absorbance from one wavelength to another. For example, a photometric assay is described in U.S. Pat. No. 4,235,961 (issued Nov. 25, 1980 to Lundin) wherein reaction (1) above is combined with the following reaction (5) to produce detectable emissions of light:

$$\text{ATP} + \text{luciferin} + O_2 \xrightarrow{\text{luciferase}}$$ (5)

oxyluciferin + $CO_2$ + AMP + PPi + light wherein PPi is pyrophosphate.

More particularly, total CK or an isoenzyme, e.g. CK-MB, is determined by colorimetric means whereby an optical density change is measured at a wavelength between about 200 and about 900 nm. At wavelengths below 400 nm, the measurements are generally in the ultraviolet regions of the electromagnetic spectrum, as when NADH (i.e. nicotinamide adenine dinucleotide, reduced form) or NADPH are measured according to the following coupled enzymatic reaction schemes.

Reactions (1), (2) and (3) noted above can be used together, as described in *J. Clin. Chem. Clin. Biochem.*, 15, pp. 255-260 (1977), U.S. Pat. No. 4,220,714 (issued Sept. 2, 1980 to Meiattini et al).

A similar sequence of coupled reactions beginning with reaction (1) and using NADH in reactions (6) and (7) below is described in U.S. Pat. No. 4,352,881 (issued Oct. 5, 1982 to Inagawa et al):

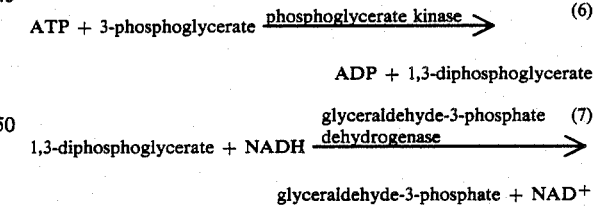

Other colorimetric assays carry either reaction (3) or (7) further by reducing a colorless tetrazolium salt and forming a colored dye according to reaction(8):

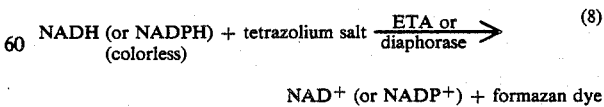

Such assays are described, for example, in U.S. Pat. Nos. 4,012,286 (issued Mar. 15, 1977 to Sanderson et al) and 4,247,633 (issued Jan. 27, 1981 to Case et al).

The reagents and enzymes needed for the assays described above are commercially available. In each case, the indicator composition comprises the nonenzymatic reagents needed for the assay.

In a preferred embodiment of the present invention, total CK, or an isoenzyme, CK-MB, activity is determined by the following sequence of reactions:

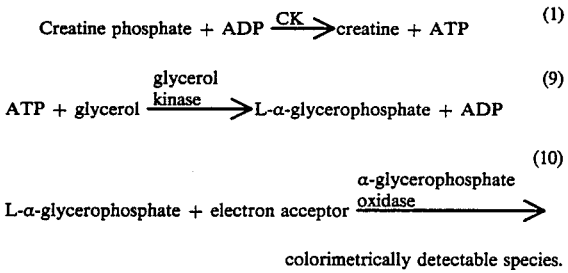

In these combined reactions, the rate of formation of the colorimetrically detectable species is directly proportional to the rate of creatine kinase or isoenzyme activity in the liquid sample. The details of this sequence of reactions are provided in EP application No. 116,307 (published Aug. 22, 1984) the disclosure of which is incorporated herein by reference.

The first reaction in the above-described sequence is the reaction of creatine phosphate and ADP to form creatine and ATP in the presence of creatine kinase in the aqueous liquid sample. As is well known in the art, this reaction usually proceeds in the presence of an enzyme cofactor, such as a divalent metal ion. Exemplary cofactors are described below. Creatine phosphate is a biological compound commercially available from any of a number of sources including Calbiochem (located in La Jolla, Calif.). Creatine phosphate is used in the practice of invention in an amount in excess of that needed stoichiometrically to make the reaction proceed.

ADP is the hydrolyzed form of the nucleotide ATP. ADP is readily available from a number of commercial sources, e.g. Sigma Chemical Co. (located in St. Louis, Mo.). The amount of ADP used in the assay is discussed in more detail below.

As shown in reaction (9) above, glycerol kinase catalyzes the phosphorylation of glycerol to L-α-glycerophosphate in the presence of ATP. Generally, any glycerol kinase is useful in the successful practice of the present invention although those obtained from *E. coli* and *Candida mycoderma* are preferred. Glycerol kinase enzymes from other sources are well known in the art. A complete discussion of such materials and further references to their preparation and reactivity may be found in T. E. Barman, *Enzyme Handbook*, I, Springer-Verlag, N.Y. (1969) pages 401–402. Worthington Biochemical Company (Freehold, N.J.) is a commercial source of glycerol kinase.

The glycerol useful in the practice of this invention can also be readily obtained commercially from, e.g. Eastman Organic Chemicals (Rochester, N.Y.) or prepared using techniques well known in the art. Glycerol can be provided either in free form or as a fatty acid ester of glycerol (e.g. triglycerides). Preferably, free glycerol is used in the practice of this invention.

The next step in the reaction sequence involves the oxidation of L-α-glycerophosphate oxidase and, generally, an electron acceptor to produce a colorimetrically detectable species. This species is quantitatively related to the analyte contained in the liquid sample.

L-α-glycerophosphate oxidase is a microbial enzyme which can be derived from a variety of sources. A detailed description of this enzyme and exemplary sources are provided in U.S. Pat. No. 4,241,178 (issued Dec. 23, 1980 to Esders et al). Also, the following references describe both the enzyme and useful techniques for its preparation and extraction:

Esders et al, "Purification and Properties of L-α-Glycerophosphate Oxidase from *Streptococcus faecium* ATCC 12755," *J. Biol. Chem.*, 254, pp. 2710–2715 (1979), Koditschek et al, "α-Glycerophosphate Oxidase in *Streptococcus faecium*, F 24," *Journal of Bacteriology*, 98, (3), pages 1063–1068 (1969), U.S. Pat. No. 4,166,005 (issued Aug. 28, 1979 to Masurekar et al). The enzyme can also be obtained commercially from Toyo Jozo (Shizuoka, Japan).

The oxidation of L-α-glycerophosphate occurs in the presence of an electron acceptor. Any electron acceptor which will permit oxidation of the phosphate by the oxidase with the concomitant production of a colorimetrically detectable species is suitable for use in this invention.

In one embodiment, the electron acceptor can be an indicator composition containing a chromogen (which is defined in more detail below). Such chromogen can be reduced to provide an optical density change (as defined above). The rates of any of these changes can then be monitored to measure analyte activity. Certain indophenols, potassium ferricyanide and certain tetrazolium salts are useful as electron acceptors in the practice of this embodiment. For example, 2,6-dichlorophenolindophenol alone or in combination with phenazine methosulfate or phenazine ethosulfate (i.e. an electron transfer agent), and 2-(p-indophenyl)-3-(p-nitrophenyl)-5-phenyl-2H-tetrazolium chloride either alone or in combination with phenazine methosulfate is especially useful.

In an alternative and preferred embodiment, the electron acceptor oxidizes the phosphate to produce an intermediate species which then reacts with an indicator composition to produce a colorimetrically detectable species according to the following reactions:

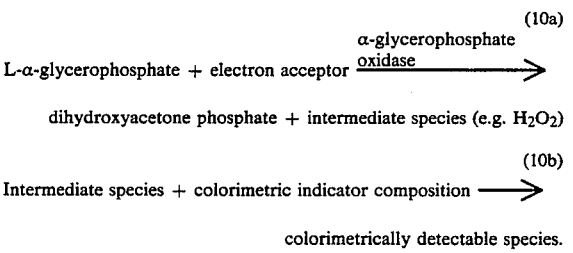

Quantification of total creatine kinase or its isoenzyme in the practice of this preferred embodiment is achieved using oxygen as the electron acceptor and a colorimetric indicator composition which comprises: (1) a substance having peroxidative activity, and (2) a chromogen. In such a case, reaction (10a) produces dihydroxyacetone phosphate and hydrogen peroxide.

Colorimetric indicator compositions which react with hydrogen peroxide in reaction (10b) are well known in the art. Generally, such compositions comprise a substance which has peroxidative activity. Preferably, this substance is peroxidase.

A peroxidase is an enzyme which will catalyze a reaction wherein hydrogen peroxide oxidizes another substance. The peroxidases are generally conjugated proteins containing iron porphyrin. Peroxidase occurs in horseradish, potatoes, figtree sap and turnips (plant peroxidase), in milk (lacto peroxidase), and in white blood corpuscles (verdo peroxidase). It also occurs in microorganisms and can be produced by fermentation. Certain synthetic peroxidases, such as those disclosed by Theorell and Maehly in *Acta chem. Scand.*, Vol. 4, pages 422–434 (1950), are also useful. A preferred peroxidase is that obtained from horseradish.

Also, useful but to a lesser extent are such substances as hemin, methemoglobin, oxyhemoglobin, hemoglobin, hemochromogen, alkaline hematin, hemin derivatives, iron sulfocyanate, iron tannate, ferrous ferrocyanide, chromic salts (such as potassium chromic sulfate) absorbed in silica gel, etc.

The colorimetric indicator composition also comprises a chromogen which is a colored or colorless substance which directly or indirectly provides a quantifiable colorimetric change the rate of which change can be quantitatively measured. The chromogen can be a dye, dye former or dye precursor. The color provided by the reaction of the chromogen is in the visible region of the electromagnetic spectrum (i.e. between about 400 and 900 nm).

Chromogens which provide color formation in the presence of hydrogen peroxide and peroxidase useful in the present invention include (with a color coupler where necessary): monoamines, diamines, phenols, polyphenols, aromatic acids, leuco dyes, triarylmethane dyes and the like.

Other chromogens which contain a material oxidizable in the presence of peroxidase and which can provide a colorimetrically detectable species include certain dye-providing compositions. In one aspect, such chromogens can include a compound that, when oxidized by peroxidase, can couple with itself or with its reduced form to provide a dye. Such autocoupling compounds include a variety of hydroxylated compounds which are well known in the art.

In another aspect, the detectable species can be provided by chromogens which include a peroxidase-oxidizable compound capable of undergoing oxidative condensation with couplers such as those containing phenolic groups or activated methylene groups, together with such a coupler. Representative of such oxidizable compounds are benzidene and its homologs, p-phenylenediamines, p-aminophenols, 4-aminoantipyrine, etc. A wide range of such couplers, including a number of autocoupling compounds, is described in the art, such as in:

*The Theory of the Photographic Process*, Mees and James (Eds), (1966), Chapter 17, Kosar, *Light-Sensitive Systems*, 1965, pages 215–249 and U.S. Pat. No. 4,321,397 (issued March 23, 1982 to Nix et al). A wide range of color couplers, including autocoupling compounds, are known in the art, including N,N-disubstituted toluidines, dihydroindoles and tetrahydroquinolines.

In still another and preferred aspect, the colorimetrically detectable species can be provided by peroxidase-induced oxidation of a leuco dye to provide the corresponding dyestuff form.

A variety of leuco dyes are useful as chromogens in the practice of this invention including those described in U.S. Pat. Nos. 4,241,178 (noted above) and 4,089,747 (issued May 16, 1978 to Bruschi), the disclosures of which are incorporated herein by reference. Leuco dyes most preferred for use in this invention are the triarylimidazoles of U.S. Pat. No. 4,089,747.

Particularly useful leuco dyes include 2-(3,5-dimethoxy-4-hydroxyphenyl)-4,5-bis(4-dimethylaminophenyl)imidazole, 2-(4-hydroxy-3-methoxyphenyl)-4,5-bi(p-dimethylamino- phenyl)-1H-imidazole and 2-(3-ethoxy-4-hydroxyphenyl-4,5-bis(p-dimethylaminohenyl)-1H-imidazole.

The amounts of the reagents, substrates and enzymes useful in the practice of this invention, including the preferred colorimetric indicator compositions, are dependent to a large extent upon the concentration of creatine kinase or isoenzyme in the sample, the sophistication of the detection apparatus, and the detectable change produced. The amounts are readily determinable by one skilled in clinical chemistry having the teachings of the many references noted above before him.

One or more adenylate kinase inhibitors can be used in the practice of this invention. Such inhibitors and the amounts generally used are known in the art. However, in a preferred embodiment, a combination of adenylate kinase (AK) inhibitors is used: (a) $P^1,P^5$-di(adenosine-5')polyphosphate, and (b) adenosine-5'-monophosphate (AMP), in proportions found to be effective to substantially reduce the activity of all (i.e. at least 99%) isoenzymes of endogenous adenylate kinase (AK) so that AK does not affect the determination of the analyte.

The polyphosphate, which can be $P^1,P^5$-di(adenosine-5')tetra-, penta- or hexaphosphate, and AMP are readily available commercially. $P^1,P^5$-di(adenosine-5')pentaphosphate is particularly useful in the practice of this invention. Further details of the use of AK inhibitors are provided in copending and commonly owned U.S. Ser. No. 729,333 filed on even date herewith by Findlay and Wu and entitled IMMUNOCHEMICAL METHOD AND ANALYTICAL COMPOSITION AND ELEMENT FOR DETERMINATION OF CREATINE KINASE-MB, the disclosure of which is incorporated herein by reference. Preferably, ADP is present in an amount of from about 0.05 to about 0.16 g/m$^2$; AMP is present in a molar ratio to ADP of at least about 10:1; and the polyphosphate is present in an amount of at least about 0.03 g/m$^2$.

The analytical element of this invention can also include other reagents or addenda generally used in total CK or CK isoenzyme determinations, including CK activators, metal ion cofactors (e.g. magnesium, calcium and iron ions), solvents, buffers, surfactants, etc. It is particularly desirable to include one or more CK activators which promote full creatine kinase activity. Such activators include mercapto-containing compounds (also known as thiol-containing or sulfhydryl compounds), such as thioglucose, dithiothreitol, dithioerythritol, mercaptoethanol, glutathione, N-acetylcysteine, cysteine, thioglycerol, thioglycolic acid, etc. in amounts known to one skilled in clinical chemistry.

The element also advantageously includes ethylenebis(oxyethylenenitrilo)tetraacetic acid in a suitable amount to improve CK sensitivity by suppressing the inhibitory effect of calcium ions.

Antibodies useful in the practice of this invention to determine a CK isoenzyme can be specific to either B or M subunits and can be generated from antisera using known procedures. The antibodies can be isolated from the antisera before use, or unpurified antisera can be used. Antisera is generally obtained from suitably innoculated monkeys, pigs, horses, goats, rabbits, rats, mice, chickens, cattle, and other animals known to be useful for this purpose. A preferred source of antibodies are suitably innoculated goats. The antibodies are generally used in an immobilized form on a suitable carrier. In the assay of this invention, one or more antibodies can be immobilized within the element itself, if desired, without any additional carrier material or added prior to or simultaneously with the test sample to the element during the assay. Further details of useful antibodies for CK-MB determinations and carrier materials are provided, for example, in U.S. Pat. Nos. 4,237,044 (issued Dec. 2, 1980 to Wurzburg et al) and 4,260,678 (issued Apr. 7, 1981 to Lepp et al), the disclosures of which are incorporated herein by reference.

The method of this invention is practiced with a dry multilayer analytical element. The element comprises a supporting material (commonly known as a support, described below) having thereon, in order and in fluid contact, a registration layer and an isotropically porous spreading layer. The reagents and/or antibodies can be incorporated into the porous spreading layer by imbibition, impregnation, coating or another suitable technique. Generally, they are incorporated into a coating composition, whereas antibodies are incorporated by imbibition or wash coating into an already coated layer. In a preferred embodiment, the antibodies are milled in dried form into a blush polymer spreading layer coating composition, as described in copending and commonly owned U.S. Ser. No. 729,332, filed on even date herewith by Findlay and Wu and entitled METHOD FOR PREPARING COATING COMPOSITIONS CONTAINING ANTISERA AND ELEMENTS CONTAINING SAME, the disclosure of which is incorporated herein by reference.

Useful absorbent materials for making porous spreading layers are insoluble and maintain their structural integrity when exposed to water or biological fluids such as whole blood or serum. Useful elements can have spreading layers prepared from paper, porous particulate structures, porous polymeric films, cellulose, wood, glass fibers, woven and nonwoven fibrous fabrics (synthetic and nonsynthetic) and the like. Useful materials and procedures for making such layers are well known in the art.

The porous spreading layer can be prepared from any suitable fibrous or non-fibrous material or mixtures of either or both. The void volume and average pore size of this layer can be varied depending upon the use intended. For example, if whole blood or other liquid samples containing high molecular weight materials are to be assayed, the void volume and average pore size are generally greater than if serum or urine is to be assayed.

Useful spreading layers can be prepared using fibrous materials, either mixed with a suitable binder material or woven into a fabric, as described in U.S. Pat. No. 4,292,272 (issued Sept. 29, 1981 to Kitajima et al). Alternatively, and preferably, the spreading layer is prepared from polymeric compositions (e.g. blush polymers) or particulate materials, e.g. beads bound together with or without binding adhesives, as described in U.S. Pat. Nos. 3,992,158 (issued Nov. 16, 1976 to Przybylowicz et al) and 4,258,001 (issued Mar. 24, 1981 to Pierce et al), the disclosures of which are incorporated herein by reference in their entirety. Other useful spreading zone materials are described in U.S. Pat. No. 4,430,436 (issued Feb. 7, 1984 to Koyama et al) and Japanese Patent Publication No. 57(1982)-101760 (published June 24, 1982). The spreading layer should be isotropically porous, meaning that the porosity is the same in each direction in the layer as caused by interconnected spaces or pores between particles, fibers, polymeric strands, etc.

The support can be any suitable dimensionally stable, and preferably, nonporous and transparent (i.e. radiation transmissive) material which transmits electromagnetic radiation of a wavelength between about 200 and about 900 nm. A support of choice for a particular element should be compatible with the intended mode of detection (fluorescence or colorimetric spectroscopy). Useful supports can be made from paper, metal foils, polystyrene, polyesters [e.g. poly(ethylene terephthalate)], polycarbonates, cellulose esters (e.g. cellulose acetate), etc.

The element of this invention has a registration layer under the porous spreading layer. The registration layer can contain one or more reagents or enzymes needed for the assay, surfactants, buffers, etc. or it can be free of such materials. It does contain one or more hydrophilic binder materials (e.g. treated or untreated gelatin and other colloidal materials, polysaccharides, vinyl pyrrolidone polymers, acrylamide polymers, etc.). Examples of other binder materials are known to one skilled in the art. Preferably, the layer contains gelatin which has been hardened with a conventional hardener.

In order to improve the stability of this element, it is critical that the registration layer contain at least about 8 g/m$^2$ (dry weight) of the binder material, and preferably at least about 10 g/m$^2$ (dry weight). As used in this disclosure and the claims, the coating coverage is determined as "dry weight" after normal coating and drying processes. However, it is known that some binder materials retain some moisture even after drying. For example, Type IV deionized gelatin, a preferred binder material, contains about 20%, by weight, of moisture in the "dry weight" coverage.

The elements can have one or more other layers, e.g. additional spreading layers, radiation-blocking or filter layers, subbing layers, barrier layers, reagent layers, etc. The layers are generally in fluid contact with each other, meaning that fluids, reagents and reaction products (e.g. color dyes) can pass or be transported between superposed regions of adjacent layers. Besides the references noted above, suitable element components are described also, for example, in U.S. Pat. No. 4,042,335 (issued Aug. 16, 1977 to Clément), U.S. Pat. No. 4,132,528 (issued Jan. 2, 1979 to Eikenberry et al), and U.S. Pat. No. 4,144,306 (issued Mar. 13, 1979 to Figueras).

A preferred embodiment of this invention is a multilayer element useful for determining CK-MB comprising a support having thereon, in order and in fluid contact, a registration layer containing an indicator composition described herein (e.g. a colorimetric indicator composition), a reagent layer containing creatine phosphate, AMP, ADP and a polyphosphate described herein, optionally a subbing layer, and a porous spreading layer which optionally contains either a CK activator or at least one antibody for the M subunits or both. The reagent layer generally contains one or more hydrophilic binder materials (e.g. gelatin, vinyl pyrrolidone polymers, acrylamide polymers, etc.) surfactants, and other addenda. The subbing layer can comprise one or more subbing materials known to one skilled in the art, e.g. vinyl pyrrolidone polymers, acrylamide polymers, and the like.

When the preferred colorimetric indicator composition described above is used, the registration layer also contains α-glycerophosphate oxidase, and the reagent layer also contains glycerol and glycerol kinase.

Optionally, this element can also include a second porous spreading layer which is the outermost layer of the element. The second porous spreading layer can be constructed of materials which are the same as or different from those in the first porous spreading layer. For example, the first spreading layer can comprise blush polymers prepared according to U.S. Pat. No. 3,992,158 (noted above) and the second spreading layer can be composed of particulate materials prepared according to U.S. Pat. No. 4,258,001 (noted above).

The elements of this invention can also contain one or more other addenda commonly put in the elements for various manufacturing or operational advantages. Such addenda include surfactants, buffers, solvents, hardeners and the like.

A variety of different elements, depending on the method of assay, can be prepared in accordance with the present invention. Elements can be configured in a variety of forms, including elongated tapes of any desired width, sheets, slides or chips.

The assay of this invention can be manual or automated. In general, in using the dry elements, total CK or CK isoenzyme determination is made by taking the element from a supply roll, chip packet or other source and physically contacting it with a sample (e.g. 1–100 μl) of the liquid to be tested. Such contact can be accomplished in any suitable manner, e.g. dipping or immersing the element into the sample or, preferably, by spotting the element by hand or machine with a drop of the sample with a suitable dispensing means.

After sample application, the element is exposed to any conditioning, such as incubation, heating or the like, that may be desirable to quicken or otherwise facilitate obtaining any test result. Prior to incubation, a CK-activator and any antibodies for the M subunits can also be added to the element individually or together if they are not incorporated within the element.

The CK or isoenzyme added to the element in the test sample then catalyzes reaction of the ADP with the creatine phosphate substrate at a rate based on the amount of analyte present in the sample. The rate of detectable change (e.g. dye formation) due to either reaction of creatine phosphate or formation of the reaction product (e.g. ATP) is quantifiable by passing the element through a zone in which suitable detection apparatus for reflection or transmission spectrophotometry, potentiometry or photometry, is provided. Suitable detection apparatus and procedures are known in the art.

In the examples which follow, illustrating the practice of this invention, the materials used were obtained as follows: Estane ™ 5715 polyurethane resin from B. F. Goodrich (Cleveland, Ohio), Triton ™ X-200E and X-405 from Rohm & Haas (Philadelphia, Pa.), magnesium acetate from Allied Chemical Corp. (Morristown, N.J.), glycerol kinase from Worthington (Freehold, N.J.), AMP, ADP and DAPP from Sigma Chemical Co. (St. Louis, Mo.), creatine phosphate from Calbiochem (San Diego, Calif.), Alkanol XC ™ from DuPont (Wilmington, Del.), horseradish peroxidase from Miles Laboratories (Elkhart, Ind.), α-glycerophosphate oxidase from Toyo Jozo (Shizuoka-Keu, Japan), and the remainder either from Eastman Organic Chemicals (Rochester, N.Y.) or prepared using conventional procedures and starting materials.

As used in the context of this disclosure and the claims, I.U. represents the International Unit for enzyme activity defined as one I.U. being the amount of enzyme activity required to catalyze the conversion of 1 micromole of substrate per minute under standard pH and temperature conditions for the enzyme.

EXAMPLE 1

Assay of Creatine Kinase-MB

In this example, CK-MB was determined using a multilayer analytical element of this invention. This determination was compared to that made with an analytical element outside the scope of this invention.

The tested elements had the general format and components shown below. Control element A was similarly tested. It was prepared like the elements currently sold commercially for total creatine kinase except that they also contained anti-CK-MM antibodies in the spreading layer. The Control element was like the element of this invention except that its registration layer had a gelatin binder coverage of 5.4 g/m$^2$ (dry coverage) whereas the element of this invention contained 10.8 g/m$^2$ (dry coverage) of gelatin in the registration layer.

The antisera was ball milled into the blush polymer coating composition used to form the porous spreading layer of each element, according to the disclosure of U.S. Ser. No. 729,332, noted above.

| | | |
|---|---|---|
| Spreading Layer | Goat anti-human CK-MM | 5,000–300,000 U/m$^2$** |
| | TiO$_2$ | 20–80 g/m$^2$ |
| | Cellulose acetate | 2–10 g/m$^2$ |
| | Estane ™ 5715 resin | 1–4 g/m$^2$ |
| | N—acetyl-L-cysteine | 0.2–0.6 g/m$^2$ |
| | Triton ™ X-405 surfactant | 0.5–3 g/m$^2$ |
| | Ethylenebis(oxyethylene-nitrilo)tetraacetic acid | 0.2–0.8 g/m$^2$ |
| Subbing Layer | Poly(N—isopropylacrylamide) | 0.2–0.6 g/m$^2$ |
| Reagent Layer | Gelatin (Hardened) | 2–8 g/m$^2$ |
| | Magnesium acetate | 0.2–2 g/m$^2$ |
| | Triton ™ X-200E surfactant | 0.005–0.5 g/m$^2$ |
| | Adenosine-5'-diphosphate (ADP) | 0.04–0.2 g/m$^2$ |
| | Glycerol kinase | 2,000–10,000 I.U./m$^2$ |
| | Adenosine-5'-monophosphate (AMP) | 0.2–2 g/m$^2$ |
| | Creatine phosphate | 1–4 g/m$^2$ |
| | P$^1$,P$^5$-di(adenosine-5')-pentaphosphate (DAPP) | 0.01–0.1 g/m$^2$ |
| | Glycerol | 0.1–0.3 g/m$^2$ |
| | 2-[Bis(2-hydroxyethyl)imino]-2-(hydroxymethyl)-1,3-propanediol | 1–5 g/m$^2$ |
| Registration Layer | Gelatin (Hardened) | 10.8 g/m$^2$ |
| | 2-[Bis(2-hydroxyethyl)imino]-2-(hydroxymethyl)-1,3-propanediol | 1–5 g/m$^2$ |
| | Alkanol XC ™ surfactant | 0.1–0.5 g/m$^2$ |
| | Peroxidase | 10,000–50,000 I.U./m$^2$ |
| | 2-(3,5-dimethoxy-4-hydroxyphenyl)-4,5-bis(4-dimethylaminophenyl)imidazole | 0.1–0.3 g/m$^2$ |
| | Ascorbic acid oxidase | 6,000–12,000 I.U./m$^2$ |
| | L-α-Glycerophosphate | 1,000–10,000 I.U./m$^2$ |
| | Glycolic acid | 0.1–0.5 g/m$^2$ |
| | 5,5-Dimethyl-1,3-cyclohexanedione | 0.01–5 g/m$^2$ |
| | Triton ™ X-200E surfactant | 0.05–1 g/m$^2$ |
| | 2,4-Di-n-pentylphenol | 1–3 g/m$^2$ |
| | Poly(ethylene terephthalate) | |

-continued

| Support |
|---|
| **The antisera level is given in Units (U) which are defined by the titer assay: (50% inhibition titer) (ml/0.093 m$^2$) = U/m$^2$. |

The elements were tested for stability in the following manner. Both elements were kept at either 25° C. and 50% relative humidity or −18° C. and 15% relative humidity for 11 days. For each element, percent sensitivity retained (% sens. ret.) was calculated by measuring the rate difference in isoenzyme activity determined with high and low level CK-MB fluids for the elements kept in high humidity compared to the elements kept in low humidity. In other words, % sens, ret, equals:

$$[(Rate_2 - Rate_1) \text{ at high humidity} \div (Rate_2 - Rate_1) \text{ at low humidity}] \times 100$$

wherein

Rate$_2$ is the isoenzyme activity determined using a fluid containing about 178 I.U./l of CK-MB, and Rate$_1$ is the isoenzyme activity determined using a fluid containing about 12 I.U./l CK-MB.

High humidity is at least 50% relative humidity (at 25° C.), and low humidity is no greater than 15% relative humidity (at −18° C.). The CK-MB fluids were spotted onto the element spreading layers, and the element response was monitored using a modified conventional spectrophotometer at 37° C. after 6 minutes.

Table I below summarizes the stability data obtained. The element of the present invention having a greater amount of binder material in the registration was significantly more stable under the high humidity keeping conditions than Control element A of the prior art.

TABLE I

| Element | % Sens. Ret. |
|---|---|
| Control A | 73 |
| Example 1 | 93 |

EXAMPLE 2

Determination of Creatine Kinase-MB Using Wash Coated Antisera

An analytical element was prepared and tested according to Example 1 except that the keeping tests were for seven days, and the antisera was wash coated into the already coated and dried porous spreading layer of the element. A Control element B was similarly prepared and tested. The Control element contained 5.4 g/m$^2$ (dry coverage) of gelatin binder in the registration layer whereas the element of this invention contained 10.4 g/m$^2$ (dry coverage) of binder in that layer. Table II below summarizes the stability test results for both elements. It can be seen that the element of this invention exhibited improved stability over Control element B.

TABLE II

| Element | % Sens. Ret. |
|---|---|
| Control B | 36 |
| Example 2 | 42 |

EXAMPLE 3

Determination of Creatine Kinase-MB Using Element Having Beaded Spreading Layer

An analytical element useful for the determination of creatine kinase-MB was prepared similar to that of Example 1 except that the porous spreading layer was a beaded structure having the following composition:

poly(vinyl toluene-co-p-t-butylstyrene-co-methacrylic acid)(61:37:2, weight ratio) beads, poly(methyl acrylate-co-2-acrylamido-2-methylpropane sulfonic acid-co-2-acetoacetoxyethyl methacrylate) (85:10:5 weight ratio) adhesive, Zonyl FSN ™ surfactant, N-acetylcysteine and antisera.

The registration layer contained 10.8 g/m$^2$ (dry coverage) of Type IV deionized gelatin binder.

Control element C was similarly prepared except that it contained only 5.4 g/m$^2$ (dry coverage) of gelatin binder in the registration layer.

Table III below summarizes the stability data obtained for the elements according to the procedure described in Example 1. It can be seen that the element of this invention had significantly greater stability over Control element C.

TABLE III

| Element | % Sens. Ret. |
|---|---|
| Control C | 56 |
| Example 3 | 92 |

EXAMPLE 4

Determination of Total Creatine Kinase

An analytical element for the determination of total creatine kinase was prepared and tested according to the procedure of Example 1 except that the antisera was omitted. This element contained 10 8 g/m$^2$ (dry coverage) gelatin binder in the registration layer. Control element D was similarly prepared and tested. This element is like that currently sold for total CK assay by Eastman Kodak Company (Rochester, N.Y.). It contained only 5.4 g/m$^2$ (dry coverage) of gelatin binder in the registration layer. Table IV below summarizes the stability test results obtained according to the procedure of Example 1 except that the test fluids contained more than one CK isoenzyme. It can be seen that the element of this invention had significantly improved stability over Control element D of the prior art.

TABLE IV

| Element | % Sens. Ret. |
|---|---|
| Control D | 20 |
| Example 4 | 82 |

The invention has been described in detail with particular reference to preferred embodiments thereof, but it will be understood that variations and modifications can be effected within the spirit and scope of the invention.

We claim:

1. A multilayer analytical element for the determination of total creatine kinase or a creatine kinase isoenzyme, said element comprising three or more layers and containing in one or more of said layers, a substrate for creatine kinase, said element also comprising a support having thereon, a registration layer containing a binder material at a coverage of at least about 8 g/m² and an indicator composition which provides a detectable change in response to the reaction of said substrate with said creatine kinase or said isoenzyme, a reagent layer, and an isotropically porous spreading layer containing an activator for creatine kinase, said layers being in order from said support and in fluid contact.

2. The element of claim 1 wherein said indicator composition provides an optical density change in response to adenosine-5'-triphosphate or its reaction product.

3. The element of claim 1 wherein said binder material is present at a coverage of at least about 10 g/m².

4. The element of claim 1 wherein said binder material is gelatin.

5. The element of claim 1 wherein said reagent layer contains creatine phosphate.

6. The element of claim 1 wherein said reagent layer comprises adenosine-5'-monophosphate, adenosine-5'-diphosphate and $P^1$, $P^5$-di(adenosine-5')pentaphosphate.

7. The element of claim 1 wherein said porous spreading layer contains one or more antibodies for an isoenzyme of creatine kinase.

8. A multilayer analytical element for the determination of creatine kinase-MB, said element comprising a nonporous support having thereon, in order from said support and in fluid contact, a registration layer containing a binder material at a coverage of at least about 10 g/m², and an indicator composition which provides an optical density change in response to adenosine-5'-triphosphate or its reaction product, a reagent layer containing creatine phosphate, adenosine-5'-diphosphate, adenosine-5'-monophosphate and $P^1,P^5$-di(adenosine-5')pentaphosphate, and an isotropically porous spreading layer containing an activator for creatine kinase and one or more antibodies for creatine kinase-MM.

9. The element of claim 8 wherein said registration layer binding material is gelatin.

10. The element of claim 8 wherein said adenosine-5'-diphosphate is present in an amount of from about 0.05 to about 0.16 g/m², said adenosine-5'-monophosphate is present in a molar ratio to adenosine-5'-diphosphate of at least about 10:1, and $P^1,P^5$-di(adenosine-5')pentaphosphate is present in an amount of at least about 0.03 g/m².

11. The element of claim 8 wherein said registration layer contains α-glycerophosphate oxidase, said reagent layer contains glycerol and glycerol kinase, and said indicator composition comprises a substance having peroxidative activity and a leuco dye.

12. A method for the determination of total creatine kinase or a creatine kinase isoenzyme in an aqueous liquid, said method comprising the steps of:

(A) contacting a sample of said liquid with an analytical element comprising three of more layers and containing in one or more of said layers, a substrate for creatine kinase, said element also comprising a support having thereon, a registration layer containing a binder material at a coverage of at least about 8 g/m² and an indicator composition which provides a detectable change in response to the reaction of said substrate with said creatine kinase or said isoenzyme, a reagent layer, and an isotropically porous spreading layer containing an activator for creatine kinase, said layers being in order from said support and in fluid contact, and (B) determining the resulting detectable change.

13. The method of claim 12 for the determination of creatine kinase-MB wherein said contact is carried out in the presence of one or more antibodies for creatine kinase-MM.

14. The method of claim 12 wherein said detectable change is an optical density change.

15. The method of claim 14 wherein said optical density change is a colorimetric change.

16. A method for the determination of creatine kinase-MB in an aqueous liquid, said method comprising the steps of:

(A) contacting a sample of said liquid with the analytical element of claim 8, and (B) determining the resulting optical density change.

17. The method of claim 16 wherein said element comprises adensoine-5'-diphosphate present in an amount of from about 0.05 to about 0.16 g/m², adensoine-5'-monophosphate present in a molar ratio to adenosine-5'-diphosphate of at least about 10:1, and $P^1$, $P^5$-di(adenosine-5') pentaphosphate present in an amount of at least about 0.03 g/m².

18. The method of claim 16 wherein said element has α-glycerophosphate in the registration layer, glycerol and glycerol kinase in the reagent layer, and the indicator composition comprises a substance having peroxidative activity and a leuco dye.

19. The method of claim 16 wherein said element contains gelatin as said binder material in said registration layer.

* * * * *